(12) United States Patent
Shelley et al.

(10) Patent No.: US 7,956,327 B2
(45) Date of Patent: Jun. 7, 2011

(54) METHOD FOR DETERMINING DEGREE OF AGING OF A POLYMER RESIN MATERIAL

(75) Inventors: Paul H. Shelley, Lakewood, WA (US); Gregory J. Werner, Puyallup, WA (US); Joe Baratto, Seattle, WA (US)

(73) Assignee: The Boeing Company, Chicago, IL (US)

( * ) Notice: Subject to any disclaimer, the term of this patent is extended or adjusted under 35 U.S.C. 154(b) by 451 days.

(21) Appl. No.: 12/235,399

(22) Filed: Sep. 22, 2008

(65) Prior Publication Data

US 2010/0276578 A1    Nov. 4, 2010

(51) Int. Cl.
*G01J 5/02*    (2006.01)
(52) U.S. Cl. ............... 250/339.11; 250/339.09
(58) Field of Classification Search ............. 250/339.09, 250/339.11
See application file for complete search history.

(56) References Cited

U.S. PATENT DOCUMENTS

| | | | | |
|---|---|---|---|---|
| 4,159,894 | A * | 7/1979 | Hu | 436/60 |
| 5,872,447 | A * | 2/1999 | Hager, III | 324/71.1 |
| 6,784,428 | B2 * | 8/2004 | Rabolt et al. | 250/339.02 |
| 6,903,339 | B2 | 6/2005 | Shelley et al. | |
| 6,906,327 | B2 * | 6/2005 | Shelley et al. | 250/339.01 |
| 7,115,869 | B2 | 10/2006 | Shelley et al. | |
| 7,223,977 | B2 | 5/2007 | Shelley et al. | |
| 2010/0038544 | A1 * | 2/2010 | Shelley et al. | 250/339.09 |

* cited by examiner

*Primary Examiner* — David P Porta
*Assistant Examiner* — Mindy Vu
(74) *Attorney, Agent, or Firm* — Tung & Associates (57) ABSTRACT

A method of determining degree of aging of an incompletely cured polymer resin material collecting IR spectra on a series of standards with carefully controlled aging time and data collected at appropriate time intervals with the standard LC method for determining cure condition of the material, using said spectra and LC data to make a multivariate calibration model and using said model to predict the cure condition of uncured samples of interest.

23 Claims, 5 Drawing Sheets

METHOD FOR DETERMINING DEGREE OF AGING OF A POLYMER RESIN MATERIAL

FIELD OF THE INVENTION

This disclosure generally relates to Infrared (IR) measurement methods and apparatus, and more particularly provides a method for performing non-destructive IR spectroscopy measurements of surface characteristics of materials including determining a degree of aging or curing of a polymer resin material, including an initially uncured polymer resin material impregnated in sheet material used in composite lamination to form composite materials, such as pre-impregnated carbon fiber reinforced sheet material, including as part of an aircraft manufacturing, assembly, maintenance, or repair process. Such materials are normally kept in a freezer to prevent the cure from advancing and once out of the freezer the cure does advance at room temperature.

BACKGROUND OF THE INVENTION

IR spectroscopy measurements may be useful for a variety of purposes including aerospace, automotive and industrial applications, as well as biological and bio-medical applications. For example, infrared (IR) radiation is readily absorbed by materials in association with relative motions (vibrations) of atoms such as carbon, hydrogen, oxygen and nitrogen. As such, IR spectroscopy measurements may indicate a condition of a wide variety of organic as well as inorganic materials.

Frequently, it is desirable to maintain a polymer resin material in a known state of cure (e.g., a known degree of polymer cross-linking) including a relatively uncured state prior to use of the polymer resin material. For example, an initially uncured (unaged) polymer resin material may tend to lose desirable properties, such as adhesiveness and flexibility, the longer the polymer resin material is removed from a freezer and exposed to the environment (aged), including storage under controlled environmental conditions, such controlled lighting and temperature conditions. The loss of desirable properties is related to complex chemical reactions that take place in the polymer resin material over time including polymeric cross-linking chemical reactions.

For example, certain polymer composite structural materials, such as those used in aircraft, are pre-impregnated (prepreg) with relatively uncured polymer resin material, which must then be maintained in a controlled environment, such as a frozen environment, prior to use in the formation of a laminated composite material structural part. The controlled environment is necessary in order to maintain the relatively uncured state and associated adhesive properties of the prepreg material which are important in forming composite laminates to build the structural part.

One problem with quality control of initially relatively uncured polymer resin materials, such as adhesives, surfacing materials, and laminating materials, is that prior art methods of determining a degree of aging or curing of the polymer resin material, requires removing samples of the material, thus, destroying a portion of the sample, and performing ex-situ time consuming laboratory analysis, during which time, the polymer resin material will age further. The state of cure for pre-preg materials is currently measured with liquid chromatography (LC), which requires a solvent extraction of the pre-preg and the proper laboratory equipment to perform the LC analysis. Current specifications for allowable pre-preg aging are based on the liquid chromatography analysis method with a ratio of two chromatogram peaks.

Other infrared(IR) non-destructive methods in the prior art used to measure the properties of thin films includes using IR absorbance to determine the amount of a chromated conversion coating on a metallic substrate (U.S. Pat. No. 6,794,631), determining the amount of an anodize coating on a metallic substrate, (U.S. Pat. No. 6,784,431), determining an amount of chemical cure and amount of surface contamination with filter infrared spectroscopy (U.S. Pat. No. 6,906,327), determining the amount/thickness of an opaque coating on a substrate (U.S. Pat. No. 6,903,339) and (U.S. Pat. No. 7,223,977), and determining an amount of heat damage to a resin-fiber composite substrate (U.S. Pat. No. 7,115,869), all of which are fully incorporated by reference herein.

None of the above methods and associated devices, however, disclose a method or device that is suitable for performing in-situ, real time IR spectroscopy including determining a degree of chemical curing (aging) of a polymer resin material, particularly where a portable, real-time capability is desirable, such as in aircraft manufacturing, assembly, maintenance, and repair of aircraft.

Thus, there is a continuing need for improved IR non-destructive testing methods including a method that is suitable for performing IR spectroscopy to determine a degree of chemical curing (aging) of a polymer resin material, including a portable, real-time IR spectroscopic method, including advantageously useable in aircraft manufacturing, assembly, maintenance, and repair of aircraft.

Therefore it is an object of the invention to provide a method that is suitable for performing IR spectroscopy to determine a degree of chemical curing (aging) of a polymer resin material, including a portable, real-time IR spectroscopic method, including advantageously useable in aircraft manufacturing, assembly, maintenance, and repair of aircraft.

SUMMARY OF THE INVENTION

In one embodiment a method of determining degree of aging of an incompletely cured polymer resin material is provided, the method including irradiating said polymer resin material with infrared energy over a spectrum of wavelengths; detecting said infrared energy reflected from said polymer resin over said spectrum of wavelengths; performing multivariate analysis on the spectrum of said reflected infrared energy; comparing results of said multivariate analysis with a predetermined calibration between model infrared energy spectra including said spectrum of wavelengths collected from a plurality of model polymer resin samples, said model polymer resin samples each including a different degree of aging; and, determining a degree of aging of said polymer resin material level based on said predetermined calibration. Ideally the calibration is based on the aging data of the model resin samples using the liquid chromatography method for determining the age of the samples.

These and other objects, aspects and features of the invention will be better understood from a detailed description of the preferred embodiments of the invention which are further described below in conjunction with the accompanying Figures.

DETAILED DESCRIPTION OF THE PREFERRED EMBODIMENT

The present invention achieves the foregoing objects, aspects and features by providing a method of non-destructively determining the degree of chemical curing (aging) of an initially relatively uncured polymer resin (pre-preg) material where the method may be accomplished by making an infrared (IR) spectroscopy measurement with an IR spectrometer on a series of pre-preg aging standards, preferably a portable IR spectrometer, and performing a multivariate calibration on the collected IR spectra to the standard LC data for the aging material and using the calibration model to predict the condition of pre-preg materials in question to determine a degree of chemical curing (aging) of the initially relatively uncured polymer resin material including as part of an manufacturing, assembly, maintenance, or repair process of an aircraft.

It will be appreciated that although the invention is particularly explained with reference to using IR spectroscopy to determine a degree of chemical curing (aging) of an initially relatively uncured polymer resin material, such as polymer resin material pre-impregnated in a polymer composite material used in portions of aircraft to determine whether the material possesses acceptable properties, such as adhesiveness in composite laminate formation, that the invention may additionally be advantageously used to determine a degree of chemical curing (aging) of an initially relatively uncured polymer resin material in general, including with respect to organic adhesives in general, and with respect to organic surfacing materials in general.

It will be appreciated that polymer resin material may show different degrees of aging where a relatively unaged (uncured) polymer resin material may include an organic polymeric material that has not yet undergone sufficient chemical reactions to result in a relatively hardened (at room temperature) aged (cured) state, including substantially completed polymer cross-linking reactions, and where a relatively unaged polymer resin material may be relatively flexible at room temperature compared to a relatively aged polymer resin material. Aged composite pre-preg materials lose flexibility and the ability to have the layer applied over them to adhere properly. This can create interlaminar weakness in built up composite structure.

While either a portable or non-portable IR spectrometer may be used to carry out the IR spectroscopy measurements according to the present invention, and the spectrum of wavelengths used to make the IR spectroscopy measurements may include all or a portion of the wavelengths between about 2.5 to 25 microns, in a preferred embodiment, a hand-held portable spectrometer capable of performing near-IR and/or Fourier Transform infrared (FT-IR) spectroscopy measurements is used to perform the IR spectroscopy measurements according to the present invention. The FT-IR spectrometer may further have the capability (with sample interfaces) for performing measurements such as attenuated total reflection (ATR) (e.g., diamond crystal reflector) and specular-reflectance measurements.

The hand-held portable IR spectrometer may have the capability to supply source IR energy to a sample at a predetermined incident angle between about 30 to about 60 degrees, and collect reflected light from the sample through a broad range of angles which may include or exclude the incident angle. The hand-held portable IR device may have the ability to make diffuse reflectance IR spectroscopic measurements (also referred to as an external reflectance IR spectroscopic measurement) (e.g., near-IR), specular-diffuse reflectance (e.g., FT-IR), or specular reflectance (e.g., FT-IR) spectroscopic measurements.

Figure 1A:
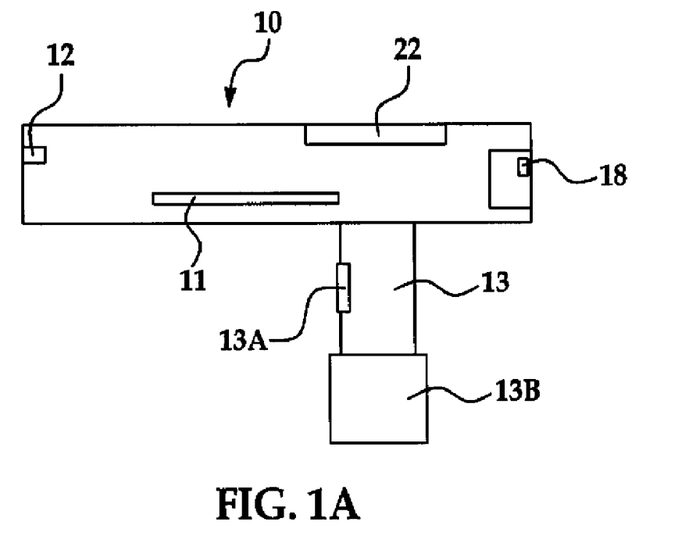
FIGS. 1A and 1B are schematic diagrams of exemplary hand-held portable IR spectrometers suitably used to make IR spectroscopy measurements according to embodiments of the invention.

Referring to FIG. 1A is shown a side view of an exemplary portable (handheld) IR spectrometer 10 for performing near-IR spectroscopy measurements according to an embodiment of the invention. By the term portable (handheld) is meant an instrument that may be easily carried and picked up and moved about to make IR spectroscopy measurements by an average person, e.g., has a weight of less than about 8 pounds and may be hand-held and aimed (or held against) a location on the measurement surface to make a spot-size measurement.

The portable IR spectrometer 10 preferably includes a microprocessor and memory (e.g. micro-processor board 11) and may be interfaced (placed in communicated with) with other computing devices (e.g., USB port 18). The portable IR spectrometer 10 may be supplied power by one or more batteries (e.g., 13B in handle portion 13). The portable IR spectrometer 10 is preferably programmable and/or capable of accepting, storing, and executing preprogrammed instructions for carrying out IR spectroscopy measurements. The portable IR spectrometer 10 preferably has the capability to provide incident IR light (energy) to a sample (not shown) and collect reflected IR spectra from the sample over all or portions of an operating wavelength range (e.g., 2.5 microns 25 microns or 4000 to 400 wavenumbers), through IR transparent window e.g., 12, and to store the spectra and perform mathematical manipulation of the data comprising the spectra including performing multivariate analysis of the spectra.

The portable IR spectrometer 10 may include a triggering device e.g. 13A on handle portion 13 for triggering an IR spectroscopy or the IR spectroscopy measurement may be alternately triggered e.g., by softkeys on an interactive LCD touchscreen 22. It will be appreciated that the portable IR spectrometer 10 may be of any suitable ergonomic shape to enhance the portability and ease of holding and manipulating the spectrometer to carryout hand-held IR spectroscopy measurements.

Figure 1B:
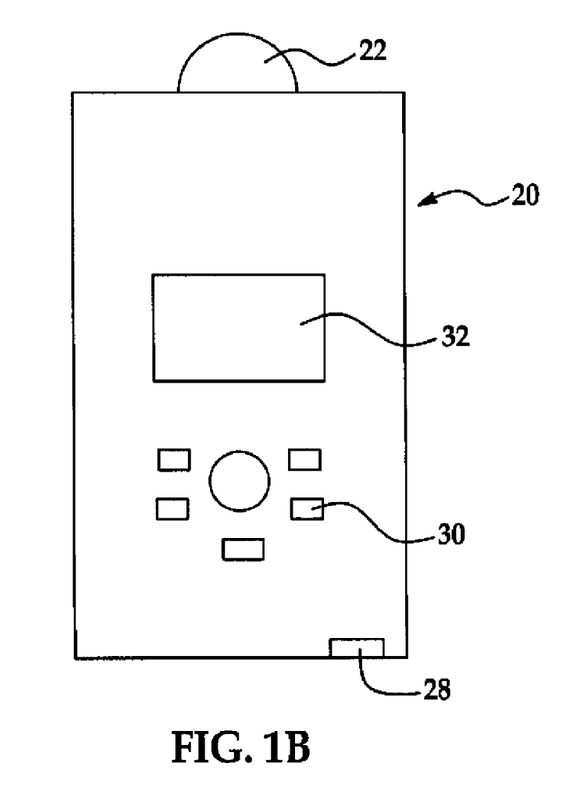

Referring to FIG. 1B is shown a top view of a second portable (handheld) IR spectrometer 20 for performing FT-IR spectroscopy measurements according to another embodiment of the invention. The portable IR spectrometer 20 likewise, preferably has the ability to store collected IR spectra and perform mathematical manipulation of the data comprising the spectra including multivariate analysis of the spectra. The portable IR spectrometer 20 may include interactive buttons e.g., 30, and/or softkeys e.g., on an interactive LCD or LED touchscreen 32, and may include a textual display to guide the operator through an IR spectroscopy measurement process. The portable IR spectrometer 20 also preferably includes a computer processor and memory and may be interfaced (placed in communicated with) with other computing devices (e.g., USB port 28). The portable IR spectrometer 20 may be supplied power by one or more batteries. The portable IR spectrometer 20 is preferably programmable and/or capable of accepting, storing, and executing preprogrammed instructions for carrying out FT-IR spectroscopy measurements.

The FT-IR spectrometer 20 preferably has the capability to provide incident IR light (energy) and collect reflected IR spectra (e.g., through one or more IR transparent energy windows/domes e.g., 22) over a range operating wavelengths (e.g., 2.5 microns to about 25 microns, or 4000 to 400 wavenumbers). For example the incident IR energy may be provided at various incident angles to a sample and collected over a broad range of wavelengths including an incident angle. The portable FT-IR spectrometer 20 may additionally have sample interfaces as are known in the art to perform ATR and specular reflectance measurements. It will be appreciated that the portable IR spectrometer 20 may be of any suitable ergonomic shape to enhance the portability and ease of holding and manipulating the spectrometer to carryout field IR spectroscopy measurements.

In addition, suitable calibration background reference standard materials and wavelength reference standard materials may be provided for calibrating the IR spectrometers 10 or 20 prior to performing IR spectroscopy measurements according to embodiments of the invention.

In one embodiment, an IR spectrometer used to carry out an IR spectroscopy measurement according to the present invention, such as the portable IR spectrometers 10 or 20, may be provided and have stored in memory one or more reference IR spectra for use in a subsequent IR spectroscopy measurement and multivariate analysis processes where the reference IR spectra is with respect to material in a similar condition to an area of the sample with a known level (e.g. baseline) of the property to be measured, such as a degree of chemical curing (aging) of an initially relatively uncured polymer resin material.

In addition, a previously determined calibration of model IR spectra versus a degree of chemical curing (aging) of a polymer resin material may be stored in memory within the IR spectrometer. For example, the predetermined calibration may be determined by correlating a plurality model IR spectra (absorbance and/or reflectance at one or more wavelengths) collected from model samples with a known degree of chemical curing (aging) of a polymer resin material as determined by separate and independent measurements, such as chemical analysis of the polymer resin material.

In one embodiment, the separate and independent measurement to determine a degree of chemical curing of the model sample may include high pressure liquid chromatography (HPLC), a known analytical chemistry method that requires dissolving samples of the material (destructive method) and then analyzing the dissolved material to determine a chemical composition of the samples. The independently determined chemical analysis, such as by HPLC, may be further correlated with an associated physical property of the polymer resin material, such as adhesive strength or out-of-freezer time.

As such, an IR spectrometer, such as portable IR spectrometer 10 or 20, may be calibrated such that an in-situ (real-time) analysis of collected IR spectra taken from an actual sample may be performed to determine a degree of chemical curing (aging) of the polymer resin material, such as polymer composite sheet material, including resinous material impregnated carbon fiber reinforced sheet material, as a real-time quality control measure prior to using the sheet material to form composite laminate sheets. A quantified (numerical) level or qualitative level of the degree of chemical curing may be determined (e.g., acceptability on a scale of 1 to 10) may be determined in real-time by a portable IR spectrometer, such as the IR spectrometer 10 or 20, and stored and/or output. Additionally or alternatively, a pass/fail type determination (degree of chemical curing (aging) above or below an acceptable threshold value) and a resulting indication thereof may stored and/or output.

The portable IR spectrometer 10 or 20, or another IR spectrometer used to carry out IR spectroscopy measurements according to embodiments of the invention, preferably includes a computer processor capable of multivariate analysis of the IR spectra. For example, the IR spectrometer (or an associated controller) preferably has the ability to mathematically and statistically correlate and determine changes in a plurality of variables (e.g., IR spectra including reflectance at a plurality of wavelengths) with respect to one or more reference IR spectra. In addition, multivariate statistical approaches may be used to correlate the statistically determined changes in the plurality of variables (e.g., absorbance and/or reflectance at one or more wavelengths) with one or more second variables or (e.g. a change in a separately measured chemical and/or physical property of IR spectra sample material (such as chemical composition representing a degree of chemical curing (aging) of an initially relatively uncured polymer resin material). Further, the separately measured chemical property may be further cross-correlated with an associated physical property, such as adhesive strength or out-of-freezer time.

There are many suitable multivariate techniques that may be used to make an IR spectroscopy measurement according to the present invention including, but not limited to, quantification methodologies, such as, partial least squares, principal component regression ("PCR"), linear regression, multiple linear regression, stepwise linear regression, ridge regression, radial basis functions, and the like.

In addition, suitable multivariate statistical approaches include classification methodologies, such as, linear discriminant analysis ("LDA"), cluster analysis (e.g., k-means, C-means, etc., both fuzzy and hard), and neural network ("NN") analysis.

Further, it will be appreciated that there are several data processing methods that may be suitably used to in connection with suitable multivariate statistical approaches including smoothing, taking first and second derivatives of the IR spectra, and peak enhancement methods.

In addition, multivariate analysis of collected IR spectra may include the selection and clustering together of groups of wavelengths on which to perform a regression analysis to determine a corresponding change in the IR spectra (spectrum) (e.g., reflectance) with respect to reference spectra (spectrum). It will be appreciated that an individual IR spectrum may be formed from several IR spectra (e.g., by averaging techniques known in the art). In addition, the raw IR spectra may transformed into second IR spectra by taking first and/or second derivatives and performing smoothing and/or peak enhancement as well as carrying out regression analysis. For example, manipulation the raw IR spectra by smoothing algorithms prior to or following taking a first derivative and then quantifying a degree of change of the IR spectra from a reference spectrum (similarly processed) according to a regression or partial lest squares analysis may be performed.

In addition, the IR spectroscopy measurement process may include collecting reference IR spectra (including calculated absorbance and/or reflectance) which may serve as a baseline from which to determine relative changes in sample IR spectra by multivariate analysis. In addition, various processing methods as are known in the art may be used to form a single IR spectrum from a collection of a plurality of collected IR spectra, including various averaging techniques, for example to improve a signal to noise ratio, prior to carrying out multivariate analysis to determine a relative change from reference spectrum. It will be appreciated that the relative change may include changes at one or more wavelengths including clusters of wavelengths.

Figure 2A:
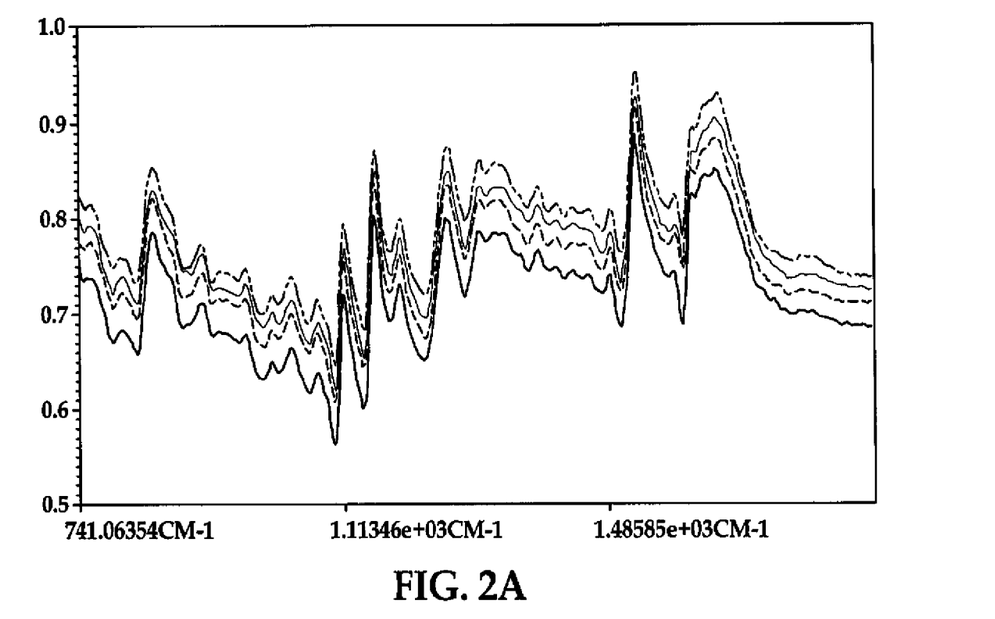
FIG. 2A are exemplary raw IR spectra for pre-preg freezer out-time samples that will be subjected to multivariate calibration to the LC data for the same samples.
Figure 2B:
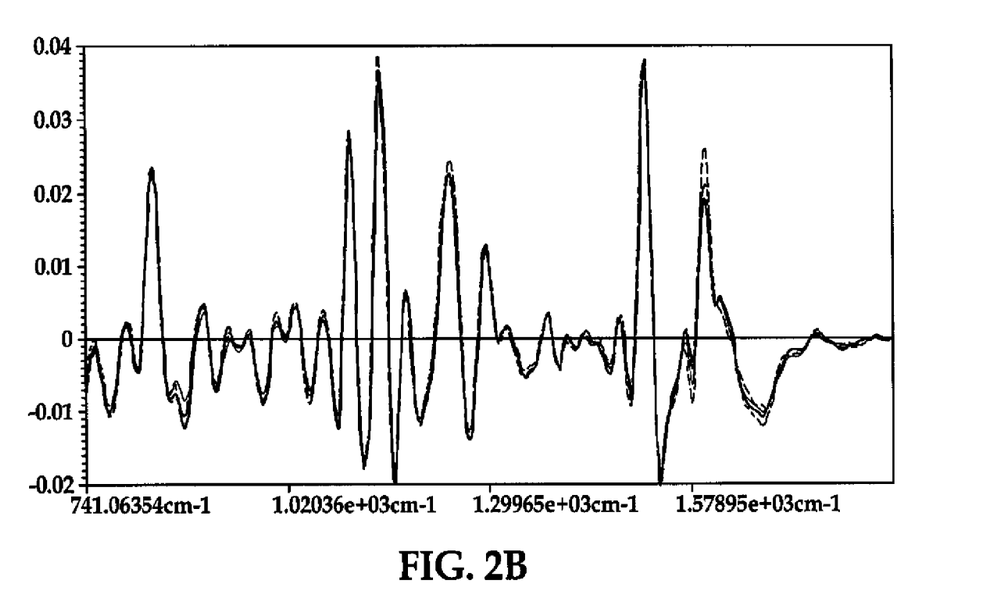
FIG. 2B shows the same spectra after pre-processing prior to multivariate calibration. Both raw and pre-processed spectra are from a selected region of the IR spectra to simplify the figures.

Referring to FIG. 2A is shown an exemplary series of raw IR spectra 200. FIG. 2B shows the same spectra following transformation of the spectra by taking a first derivative, and employing a smoothing algorithm. The pre-processed (transformed) spectra (absorbance and/or reflectance) will be used by a multivariate calibration routine which may include various techniques such as regression or partial least squares to determine a calibration model that can be used to predict the condition of samples in question.

Figure 2C:
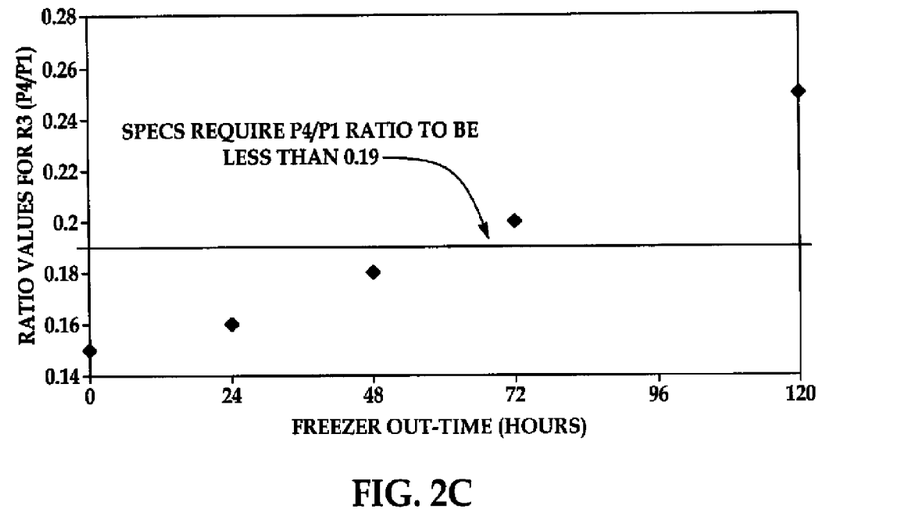
FIG. 2C shows a typical LC peak ratio plot versus pre-preg freezer out time for a series of out-time samples. This plot includes the current specified threshold limit for allowable P4/P1 ratio in the LC chromatogram.
Figure 2D:
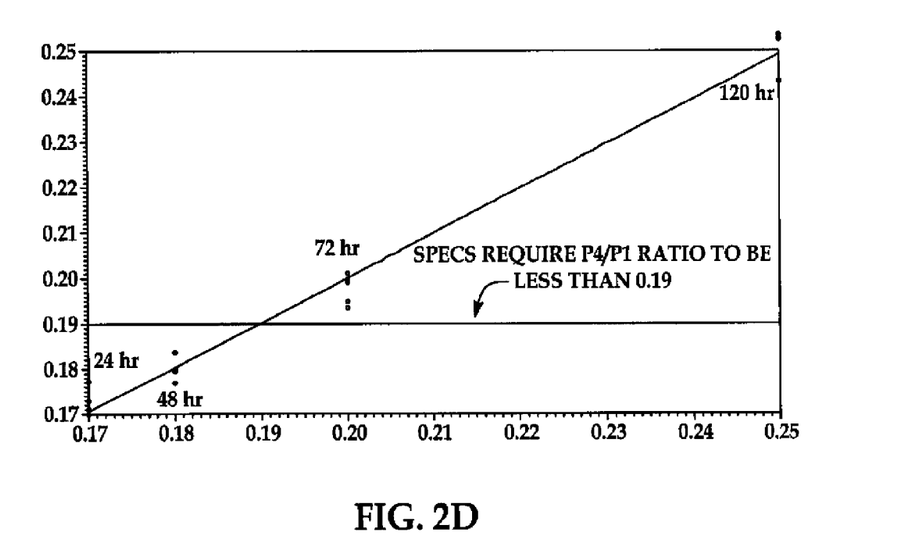
FIG. 2D shows exemplary conceptual data points of the results of a multivariate calibration of sample IR spectroscopy measurements to the LC peak ratio P4/P1 and a superimposed threshold P4/P1 value according to an embodiment of the invention. This plot is the predicted versus measured plot for the P4/P1 ratio from the multivariate calibration and shows a good calibration model for this measurement.

Referring to FIG. 2C is shown a typical LC peak ratio plot versus pre-preg freezer out time for a series of out-time samples. This plot includes the current specified threshold limit for allowable P4/P1 ratio in the LC chromatogram. FIG. 2D shows exemplary conceptual data points of the results of a multivariate calibration of sample IR spectroscopy measurements to the LC peak ratio P4/P1 and a superimposed threshold P4/P1 value according to an embodiment of the invention. This plot is the predicted versus measured plot for the P4/P1 ratio from the multivariate calibration and shows a good calibration model for this measurement.

It will be appreciated that the model IR spectra taken from a model sample of cured resinous material may be simultaneously correlated with a separately determined chemical analysis and a physical property associated with a chemical property resulting from the chemical analysis, since the chemical property may quantitatively or qualitatively determine an associated physical property such as adhesive strength or adhesiveness. For example, the horizontal axis in FIG. 2C may be simply determined to be a quality factor (e.g., adhesiveness) on an arbitrary scale (e.g., on a scale 1-10) where increasing (decreasing) values represent a decreasing (increasing) quality of the resinous organic material due to increasing levels of curing (aging).

Alternatively, the IR spectra and the chemical composition of the polymer resin material may be correlated separately from the chemical composition correlated with an associated physical property, such as adhesive strength, such that one may independently determine a degree of curing (aging) (by chemical analysis) as well as a physical property such as an adhesive strength. It will be appreciated that the chemical analysis may be separately established by one or more of any independently calibrated chemical analysis methods and that the physical property may be separately established by one or more of any independently calibrated physical property measurement methods.

In one embodiment, the polymer resin material may be a relatively uncured (e.g., viscous and flowable resinous material at room temperature) that is impregnated into a relatively cured (non-flowable/hardened) polymer composite material, such as a carbon fiber reinforced plastic sheet (ply) of material. For example the resinous material impregnated composite sheet (ply) may then be bonded to another cured or uncured composite sheet (ply) by curing the resinous material impregnated composite sheet in contact with another composite sheet of material to form a multiple-ply sheet of material.

In some embodiments, the relatively uncured polymer resin material impregnated composite material is subjected to in-situ IR spectroscopy measurements according to embodiments of the invention to determine the aging of the relatively uncured resinous material (e.g., adhesiveness) prior to using the material to bond to another composite sheet of material.

For example, by analyzing the data according to a multivariate calibration method (calibrating the IR spectra from a series of aged materials e.g., pre-preg material removed from a freezer and allowed to age in air at room temperature), and then predicting change in physical properties of material in question from the change in the sample IR spectra to determine the chemical changes in progressively cured polymer resin material, a chemical state such as degree of chemical curing (aging) and associated physical properties (e.g., adhesiveness) of the polymer resin material.

Thus, the quality or acceptability of the polymer resin material may be advantageously determined non-destructively and in-situ (without destructive collection samples for analysis elsewhere) and in real-time (results are known within a few seconds after measurement, which measurement may take from a few seconds to a few minutes) with a hand-held portable IR spectrometer prior to using the polymer resin material or material containing the polymer resin material in a manufacturing or maintenance process. It will be appreciated that the method of the present invention may be applicable to determine a curing (aging) level and therefore acceptability of any polymer resin material, such as curable organic adhesives and curable organic surfacing agents.

Figure 3:
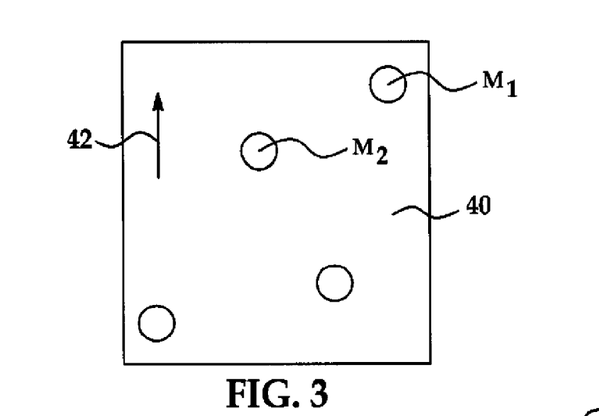
FIG. 3 shows an exemplary IR spectroscopy spot measurement process to map the aging level of a polymer pre-preg material surface according to an embodiment of the invention.

Referring to FIG. 3, an exemplary IR spectroscopy measurement process is shown including an exemplary spot measurement of a polymer resin material impregnated composite sheet. For example, following calibrating the IR spectrometer 10 or 20, a plurality of IR spectroscopy spot measurements e.g., M1, M2 (e.g., may be a defined spot size of from 1 $mm^2$-2 $cm^2$) and may be made in a predetermined sequence or randomly over a predetermined area and/or direction of the impregnated composite sheet surface 40. A degree of curing (aging) of the polymer resin material impregnated in the composite material may be determined for each measurement point e.g., by mapping of the sample measurement area with respect to each spot IR spectroscopy measurement, and/or may produce a running (cumulative) average of the measurement results. It will be appreciated that the IR spectroscopy measurement spots e.g., M1, M2, M3 may be any size and shape, may be about the same size, or may be of different sizes where and the results may be corrected for the measurement size by operator input to a spectrometer (e.g., portable IR spectrometer 10 or 20).

In one embodiment, the orientation of the portable spectrometer 10 or 20 may be important to producing reproducible measurements. For example, the portable spectrometer 10 or 20 may be consistently oriented during collection of IR spectra with respect to the direction of the fibers embedded in the composite sheet, e.g. the IR beam direction may be oriented parallel to the direction of the fibers (e.g., arrow direction 42).

Figure 4:
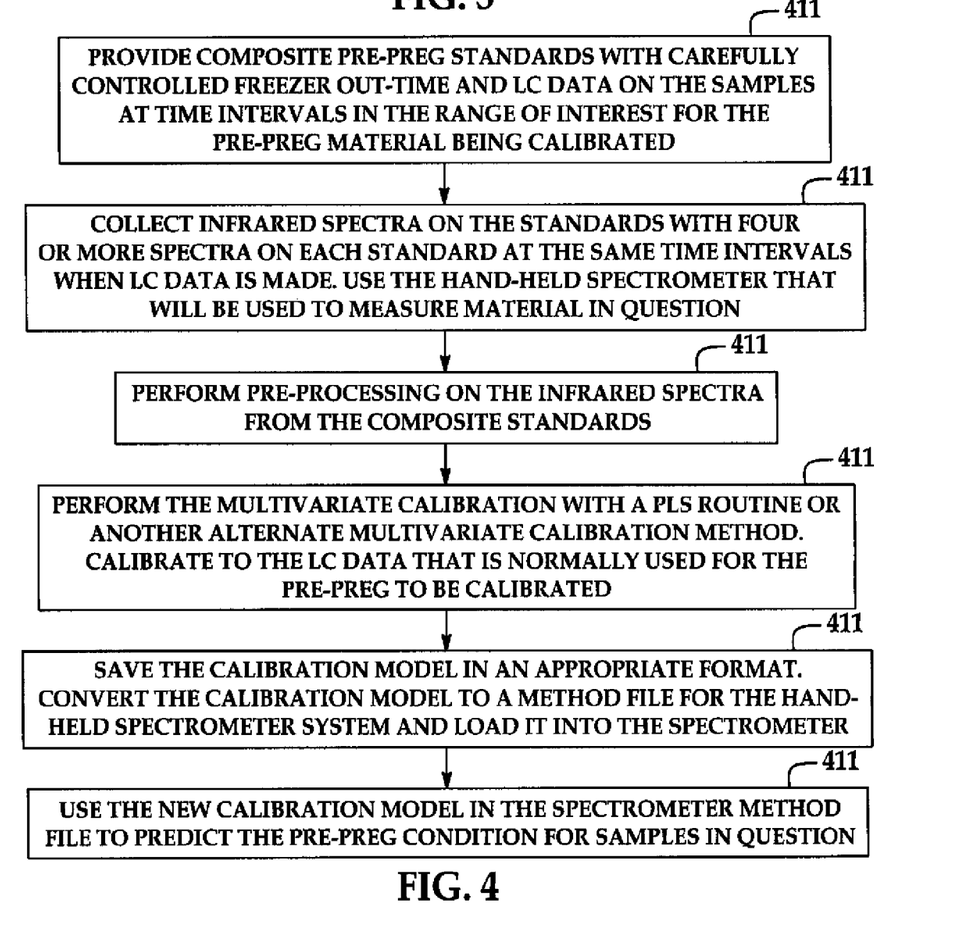
FIG. 4 is an exemplary process flow diagram including embodiments of the invention.

In an exemplary IR spectroscopy measurement process, referring to FIG. 4, in step 401 composite pre-preg standards are provided with carefully controlled freezer out-time and LC data made on the samples at time intervals the IR data will be collected and the out-time is in the range of interest for the pre-preg material being calibrated.

In step 403, the infrared spectra are collected on the standards with four or more spectra on each standard at the same time intervals when LC data is made. Use the hand-help spectrometer that will be used to measure material in question.

In step 405, data pre-processing is performed on the infrared spectra from the composite standards.

In step 407, the multivariate calibration is performed with a PLS routine or another alternate multivariate calibration method. The calibration is done with the LC data as the material variable of interest or any other physical property of the material than can be accurately measured.

In step 409, the results of the multivariate spectral calibration are saved in an appropriate format. Then the calibration model is converted to an appropriate format for the hand-held spectrometer system and load it into the spectrometer in a way that enables the spectrometer to use the model to predict the variable of interest for new samples.

In step 411, the new calibration model is used in the spectrometer method file to predict the pre-preg condition for samples in question. This allows the operator to determine whether the level of curing (aging) is acceptable or unacceptable in a pass/fail determination. (e.g., by the portable IR spectrometer 10 or 20).

Figure 5:
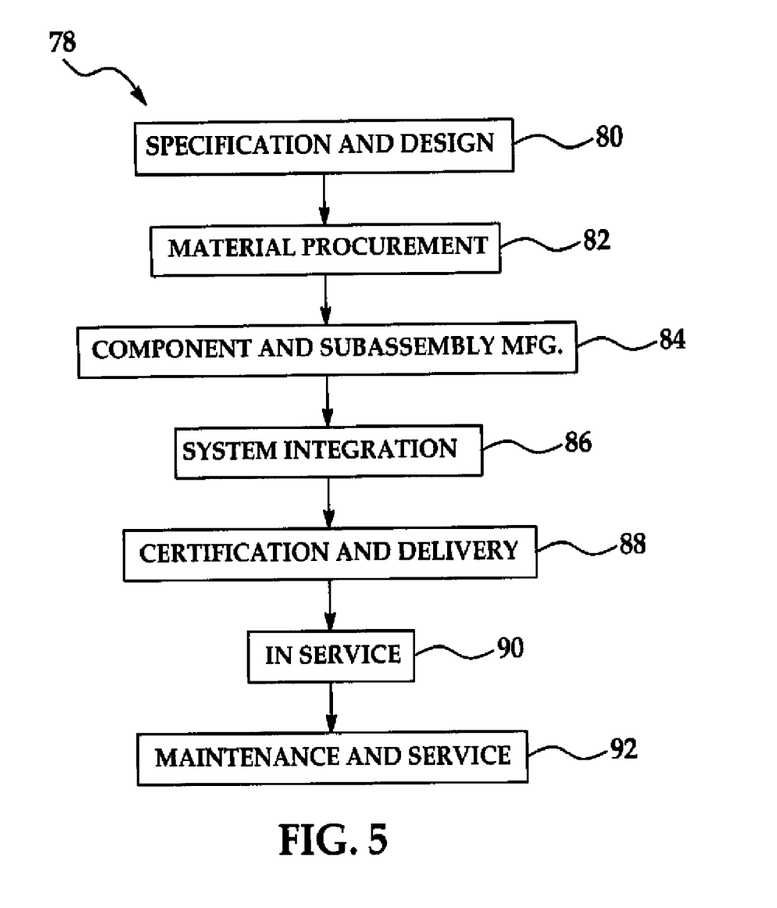
FIG. 5 is a flow diagram of an aircraft and service methodology according to an embodiment of the invention.
Figure 6:
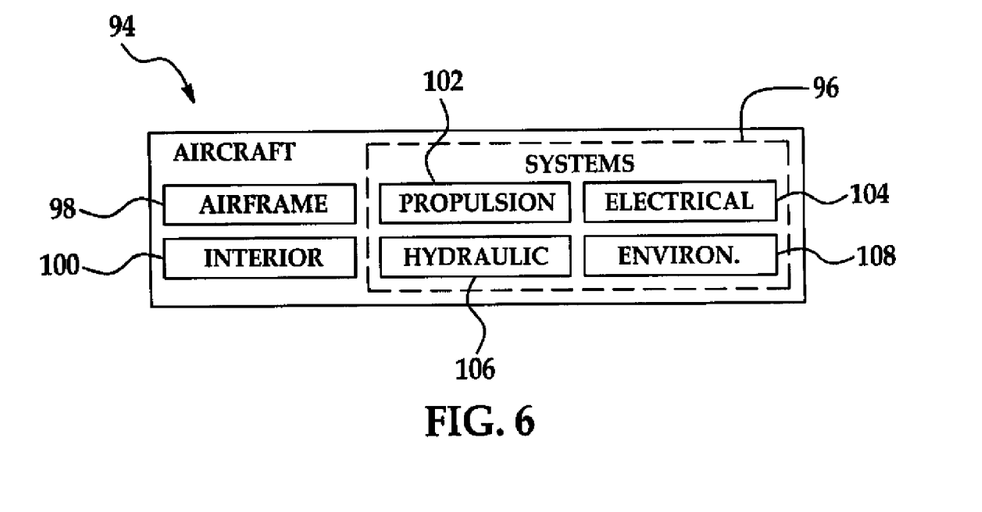
FIG. 6 is a block diagram of an aircraft according to an embodiment of the invention.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and, delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of determining degree of aging of an incompletely cured polymer resin material comprising the steps of:
   irradiating said polymer resin material with infrared energy over a spectrum of wavelengths;
   detecting said infrared energy reflected from said polymer resin over said spectrum of wavelengths;
   performing multivariate analysis on the spectrum of said reflected infrared energy;
   comparing results of said multivariate analysis with a predetermined correlation between model infrared energy spectra comprising said spectrum of wavelengths collected from a plurality of model polymer resin samples, said model polymer resin samples each comprising a different degree of aging; and,
   determining a degree of aging of said polymer resin material level based on said predetermined correlation.

2. The method of claim 1, wherein said multivariate analysis comprises multivariate statistical approaches to determine changes in absorbance and/or reflectance values at selected groups of wavelengths comprising said spectrum of wavelengths, said changes with respect to a reference spectrum.

3. The method of claim 1, wherein said incompletely cured polymer resin material comprises a material selected from the group consisting of an adhesive, a surface treating material, and a fiber resin composite material impregnated with said incompletely cured polymer resin material.

4. The method of claim 1, wherein said incompletely cured polymer resin material comprises carbon fiber reinforced composite sheet material impregnated with said incompletely cured polymer resin material.

5. The method of claim 1, wherein said different level of aging in said model polymer resin material is determined by an independent chemical analysis.

6. The method of claim 5, wherein said independent chemical analysis comprises high pressure liquid chromatography (HPLC).

7. The method of claim 1, wherein said step of irradiating said polymer resin material is preceded by collecting a reference spectrum over said spectrum of wavelengths from a reference sample wherein said polymer resin material is present at a predetermined degree of aging.

8. The method of claim 1, wherein said step of irradiating said polymer resin material is preceded by a calibration process comprising collecting reference spectra over said spectrum of wavelengths from a reference sample comprising a predetermined IR spectroscopy measurement spectrum.

9. The method of claim 1, wherein said steps comprise a near-IR measurement and said spectrum of wavelengths comprises a range of wavelengths from about 2.5 to 25 microns.

10. The method of claim 1, wherein said steps comprise a Fourier Transform (FT)-IR measurement and said spectrum of wavelengths comprises a range of wavelengths from about 2.5 to 25 microns.

11. The method of claim 1, wherein said steps are performed by a hand-held portable IR spectrometer.

12. The method of claim 1, wherein said steps comprise a process selected from the group consisting of aircraft manufacturing, aircraft assembly, aircraft maintenance, and aircraft repair.

13. A method of determining degree of aging of an incompletely cured polymer resin material comprising the steps of:
   collecting a reference spectrum over a spectrum of infrared wavelengths from a reference sample wherein said polymer resin material is present at a predetermined level of aging;
   irradiating said polymer resin material with infrared energy over a spectrum of wavelengths;
   detecting said infrared energy reflected from said ed polymer resin over said spectrum of wavelengths;
   performing multivariate analysis on the spectrum of said reflected infrared energy;
   comparing results of said multivariate analysis with a predetermined correlation between model infrared energy spectra comprising said spectrum of wavelengths collected from a plurality of model polymer resin samples, said model polymer resin samples each comprising a different level of aging; and,
   determining a level of aging of said polymer resin material based on said predetermined correlation.

14. The method of claim 13, wherein said multivariate analysis comprises multivariate statistical approaches to determine changes in absorbance and/or reflectance values at selected groups of wavelengths comprising said spectrum of wavelengths, said changes with respect to a reference spectrum.

15. The method of claim 13, wherein said incompletely cured polymer resin material comprises a material selected from the group consisting of an adhesive, a surface treating material, and a fiber resin composite material impregnated with said incompletely cured polymer resin material.

16. The method of claim 13, wherein said incompletely cured polymer resin material comprises carbon fiber reinforced composite sheet material impregnated with said incompletely cured polymer resin material.

17. The method of claim 13, wherein said different level of aging in said model polymer resin material is determined by an independent chemical analysis.

18. The method of claim 17, wherein said independent chemical analysis comprises high pressure liquid chromatography (HPLC).

19. The method of claim 13, wherein said steps comprise a near-IR measurement and said spectrum of wavelengths comprises a range of wavelengths from about 2.5 to 25 microns.

20. The method of claim 13, wherein said steps comprise a Fourier Transform (FT)-IR measurement and said spectrum of wavelengths comprises a range of wavelengths from about 2.5 to 25 microns.

21. The method of claim 13, wherein said steps are performed by a hand-held portable IR spectrometer.

22. The method of claim 13, wherein said steps comprise a process selected from the group consisting of aircraft manufacturing, aircraft assembly, aircraft maintenance, and aircraft repair.

23. A method of determining degree of aging of an incompletely cured polymer resin material impregnated into a carbon fiber reinforced composite sheet material comprising:
   irradiating said sheet material with infrared energy over a spectrum of wavelengths;
   detecting said infrared energy reflected from said sheet material over said spectrum of wavelengths;
   performing multivariate analysis on the spectrum of said reflected infrared energy;
   comparing results of said multivariate analysis with a predetermined correlation between model infrared energy spectra comprising said spectrum of wavelengths collected from a plurality of model sheet material samples, said model sheet material samples each comprising a different degree of aging of said polymer resin material; and,
   determining a degree of aging of said polymer resin material in said sheet material based on said predetermined correlation.

* * * * *